(12) United States Patent
Verschueren et al.

(10) Patent No.: US 10,029,424 B2
(45) Date of Patent: *Jul. 24, 2018

(54) CUSTOMIZED AORTIC STENT DEVICE AND METHOD OF MAKING THE SAME

(71) Applicant: MATERIALISE NV, Leuven (BE)

(72) Inventors: Peter Verschueren, Bierbeek (BE); Koen Engelborghs, Vaalbeek (BE)

(73) Assignee: Materialise, NV, Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/477,996

(22) Filed: Apr. 3, 2017

(65) Prior Publication Data

US 2017/0225398 A1 Aug. 10, 2017

Related U.S. Application Data

(63) Continuation of application No. 14/678,828, filed on Apr. 3, 2015, now Pat. No. 9,642,727, which is a (Continued)

(30) Foreign Application Priority Data

Oct. 5, 2012 (EP) .................................. 12187518

(51) Int. Cl.
| | | |
|---|---|---|
| *A61F 2/82* | (2013.01) | |
| *B29C 67/00* | (2017.01) | |
| *A61F 2/07* | (2013.01) | |
| *B33Y 10/00* | (2015.01) | |
| *B33Y 50/00* | (2015.01) | |
| *B33Y 80/00* | (2015.01) | |
| *G06F 19/00* | (2018.01) | |

(Continued)

(52) U.S. Cl.
CPC ............ *B29C 67/0088* (2013.01); *A61F 2/07* (2013.01); *A61F 2/82* (2013.01); *B33Y 10/00* (2014.12); *B33Y 50/00* (2014.12); *B33Y 80/00* (2014.12); *G06F 19/3437* (2013.01); *G16H 50/50* (2018.01); *A61F 2002/061* (2013.01); *A61F 2002/072* (2013.01); *B29L 2031/7534* (2013.01)

(58) Field of Classification Search
CPC ................. A61F 2/06; A61F 2/82; A61F 2/07
USPC ............................................... 623/1.11–1.48
See application file for complete search history.

(56) References Cited

U.S. PATENT DOCUMENTS

| 5,141,680 A | 8/1992 | Almquist et al. |
|---|---|---|
| 5,192,539 A | 3/1993 | Van Der Marel et al. |

(Continued)

FOREIGN PATENT DOCUMENTS

| DE | 2537251 A1 | 2/1977 |
|---|---|---|
| JP | 1177779 A2 | 2/2002 |

(Continued)

OTHER PUBLICATIONS

International Search Report dated Dec. 4, 2013 for related Application PCT/EP2013/070665, filed Oct. 4, 2013 and published as WO/2014/053616 on Apr. 10, 2014.

*Primary Examiner* — Suzette J Gherbi
(74) *Attorney, Agent, or Firm* — Patterson & Sheridan LLP

(57) ABSTRACT

The application provides customized aortic stent and stent graft devices and methods for the manufacture thereof. The customized aortic stent or stent graft are patient-specific in that they conform to at least part of the ascending aorta, aortic arch and/or thoracic aorta.

10 Claims, 4 Drawing Sheets

Related U.S. Application Data continuation of application No. PCT/EP2013/070665, filed on Oct. 4, 2013.

(51) Int. Cl.
*G16H 50/50* (2018.01)
*A61F 2/06* (2013.01)
*B29L 31/00* (2006.01)

(56) References Cited

U.S. PATENT DOCUMENTS

| | | | | |
|---|---|---|---|---|
| 6,143,293 | A * | 11/2000 | Weiss | A61L 27/18 |
| | | | | 424/423 |
| 2003/0003575 | A1 * | 1/2003 | Vacanti | A61K 35/44 |
| | | | | 435/371 |
| 2005/0096729 | A1 | 5/2005 | Donadio | |
| 2007/0239267 | A1 * | 10/2007 | Hendriks | A61F 2/0077 |
| | | | | 623/1.44 |
| 2008/0243284 | A1 * | 10/2008 | Grishaber | G01N 3/32 |
| | | | | 700/98 |
| 2009/0163998 | A1 | 6/2009 | Casey | |
| 2009/0292349 | A1 * | 11/2009 | Golesworthy | A61B 17/12 |
| | | | | 623/1.15 |
| 2012/0296414 | A1 * | 11/2012 | Hartley | A61F 2/07 |
| | | | | 623/1.13 |

FOREIGN PATENT DOCUMENTS

| | | |
|---|---|---|
| WO | 2000018328 A1 | 4/2000 |
| WO | 2004026178 A2 | 4/2004 |

* cited by examiner

CUSTOMIZED AORTIC STENT DEVICE AND METHOD OF MAKING THE SAME

CROSS-REFERENCE TO RELATED APPLICATIONS

This application is a continuation of U.S. application Ser. No. 14/678,828, filed Apr. 3, 2015, which is a continuation under 35 U.S.C. § 120 of International Application No. PCT/EP2013/070665, filed Oct. 4, 2013 (published in the English language by the International Bureau as International Publication No. WO/2014/053616 on Apr. 10, 2014), which claims priority to European Patent Application No. 12187518.1, filed Oct. 5, 2012. The entire contents of each of the above-referenced applications are hereby incorporated by reference.

BACKGROUND OF THE INVENTION

Field of the Invention

The application relates to customized aortic stent devices and methods for the manufacture thereof. The customized aortic stent are patient-specific. In particular embodiments, they conform to at least part of the ascending aorta, aortic arch and/or thoracic aorta.

Description of the Related Technology

Endoprostheses are a commonly used way of dealing with diseases in interventional medicine and surgery. Mesh-based endoprostheses such as stents, stent grafts, heart valve frames, etc. are of particular importance in cardiovascular applications. Also other fields of medicine make use of such endoprostheses, e.g. pulmonary tract stents, oesophagus stents, etc.

Vascular endoprostheses such as stents are tubular structures used to prop open and restore blood flow in arteries. These devices are designed such that they are deployable by catheter or similar stent delivery system, as it is desirable for stent placement procedures to be minimally invasive. Some stents are self-expandable, whereas other stents are inflated via a balloon inside the stent in order to force the stent to open.

In case of aortic aneurysm or aortic dissection vascular endoprostheses are placed near or across the aneurysm or dissection in order to redirect or reduce the blood flow into the aneurysm or dissection.

Recently, customized vascular endoprostheses, based on digital images of the endoluminal shape of the artery or the blood flow channel, have been developed. Typical customized vascular endoprostheses have a braided or V-shaped metal wire pattern which is wrapped around a customized mandrel to personalize the endoprostheses.

SUMMARY

The application provides customized vascular endoprostheses and methods for the manufacture thereof. The customized endoprostheses are patient-specific in that they conform to at least part of the vessel. In particular embodiments, the vessel is the aorta, and more particularly the endoprosthesis or part thereof conforms to at least part of the ascending aorta, aortic arch and/or thoracic aorta. Methods have been developed for the manufacturing of customized vascular endoprostheses, which methods involve the production of a 2-dimensional (2D) structure of the endoprosthesis and the use of a mold for ensuring that the 2D structure is provided into a 3D shape corresponding to the patient's anatomy.

Provided herein are methods for manufacturing a personalized vascular endoprosthesis fitting at least part of a patient's vessel anatomy. In particular embodiments, these methods comprise the steps of: a) designing a 3D model of a vascular endoprosthesis, based on a 3D image of the patient's vessel anatomy or part thereof b) transposing the 3D model to a 2D pattern for the endoprosthesis; c) manufacturing a 2D endoprosthesis structure from the 2D pattern; d) providing a mold for the vascular endoprosthesis; e) assembling the 2D endoprosthesis structure around the mold so as to obtain a 3D endoprosthesis; and f) removing the mold from the 3D endoprosthesis.

In particular embodiments, the methods envisioned herein comprise designing a 3D model of an endoprosthesis based on the patient's corrected vessel anatomy or part thereof. In the methods envisioned herein, a 2D endoprosthesis structure is wrapped around a mold to form a 3D endoprosthesis. In particular embodiments of the methods envisioned herein the step of assembling the 2D endoprosthesis structure around the mold comprises attaching one or more rigid rings onto the 2D structure.

In particular embodiments, the 3D model of the endoprosthesis is provided with grooves conform to the one or more rigid rings and/or attachment structures.

In particular embodiments, the one or more rigid rings are stitched onto the 2D structure. For this purpose, the 2D structure may comprise features such as rigid areas and/or stitch holes.

In particular embodiments, the endoprosthesis is a personalized aortic endoprosthesis which fits at least partially with the ascending aorta, the aortic arch and/or the thoracic aorta.

In particular embodiments of the methods envisioned herein, the mold used is a crushable mold. More particularly, in the methods envisioned herein, the mold comprises or consists of two or more, more particularly three or more pieces which are joined via a weakened seam, such that the mold can be broken in a controlled way, thereby allowing the endoprostheses to be removed from the mold without the need to dismantle it.

In particular embodiments, the methods envisioned herein thus comprise making a crushable mold based on the obtained 3D model of the vascular endoprosthesis.

In further particular embodiments, the mold is made by additive manufacturing.

The application also provides personalized vascular endoprostheses, such as those obtainable by the methods described herein.

The application provides personalized vascular endoprostheses comprising a proximal end, a distal end and a hollow tubular body having a central longitudinal axis, the body comprising a stent scaffold made from a polymeric material and one or more rigid ring structures encircling and attached to the stent scaffold, wherein the outer surface of the stent scaffold comprises at least one area complementary to at least part of a patient's vessel anatomy. In particular embodiments, the personalized vascular endoprosthesis comprises at least one non-circular cross-section along the length of its scaffold.

In further particular embodiments, the endoprosthesis is a personalized aortic endoprosthesis which complements at least partially with the ascending aorta, the aortic arch and/or the thoracic aorta.

The application further provides crushable molds for the manufacture of a vascular endoprosthesis, wherein the mold comprises grooves conform to one or more rigid rings for encircling the mold. The crushable molds as used in particular embodiments of the methods described herein may be used as a mandrel and can be broken into small pieces in a controlled and predefined manner, which facilitates separation of the endoprosthesis from the mandrel. Furthermore, the weakened seams of the models can be made such that they do not compromise the rigidity of the mold.

The application further provides computer-readable media adapted to perform the steps of the methods envisioned herein.

BRIEF DESCRIPTION OF THE DRAWINGS

The following description of the figures of specific embodiments is merely exemplary in nature and is not intended to limit the present teachings, their application or uses. Throughout the drawings, corresponding reference numerals indicate like or corresponding parts and features.

FIGS. 3—3D image of a customized aortic endoprosthesis as described herein.

Figure 1:
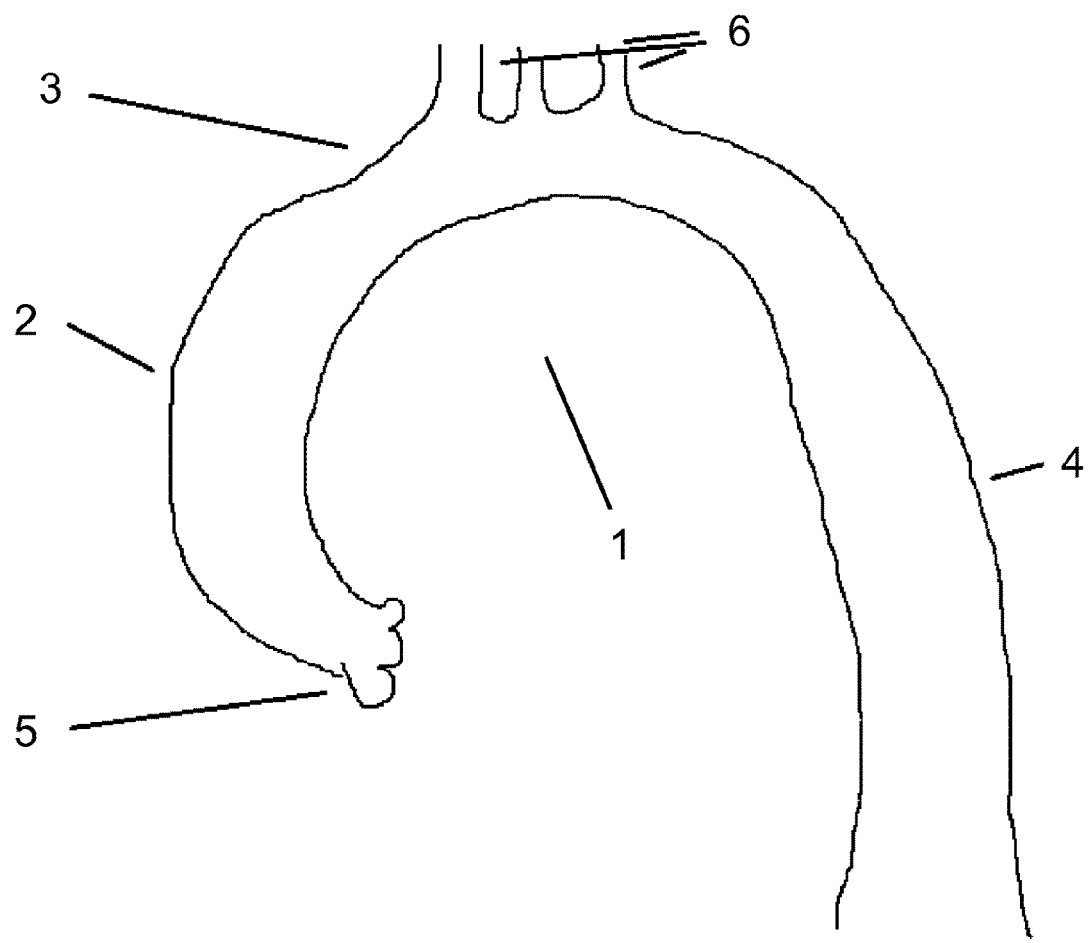
FIG. 1—Schematic representation of a patient's aorta anatomy.

In the figures, the following numbering is used: 1—aorta anatomy; 2—ascending aorta; 3—aortic arch; 4—thoracic aorta; 5—aortic valve; 6—head and neck vessels; 7—diseased part of the ascending aorta; 8—diseased part of the aortic arch going into the head and neck vessels; 10—customized aortic endoprosthesis; 11—endoprosthesis scaffold; 12—endoprosthesis rigid rings; 13—partial endoprosthesis; and 14—patient-specific features.

DETAILED DESCRIPTION OF CERTAIN INVENTIVE EMBODIMENTS

The concepts provided herein will be described with respect to particular embodiments but it is not limited thereto. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" the recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The term "about" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar such variations are appropriate to perform in the disclosure. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in this disclosure, including technical and scientific terms, have the meaning as commonly understood by one of ordinary skill in the art to which it belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the teachings provided herein, and form different embodiments, as would be understood by those in the art. For example, in the enclosed claims, any of the claimed embodiments can be used in any combination.

Provided herein are methods for manufacturing a personalized aortic endoprosthesis. The term "endoprosthesis" as used herein refers to any prosthetic device placed within the body. A "vascular endoprosthesis" as used herein refers to an endoprosthesis for use in a blood or lymph vessel of the body. The term "aortic endoprosthesis" refers to an endoprosthesis device placed within the aorta of a patient. The aorta is the largest artery in the body, originating from the left ventricle of the heart and extending down to the abdomen. The aorta distributes oxygenated blood to all parts of the body. In particular the aortic endoprosthesis is placed within the ascending aorta, the aortic arch and/or the thoracic aorta.

An endoprosthesis is typically an expandable prosthesis for implantation into a body lumen and includes devices such as stents, grafts, stent-grafts, vena cava filters, tubular expandable frameworks, heart valve frames, etc. The therapeutic objective may include but is not limited to the objective of restoring or enhancing flow of fluids through a body lumen or duct. The objective may alternatively be the prevention of flow of fluid or other material through the body lumen.

In particular, the aortic endoprostheses as described herein are of particular therapeutic use for patients suffering with complex aortic dissections and/or aneurysms that are found untreatable due to the complexity of the aneurysm or lesion. Also, due to the vicinity of the aortic valve and the branching of the head-and-neck vessels, complex aortic aneurysms and dissections occurring for instance in the ascending aorta and the aortic arch area are difficult to treat.

This is even more the case for patients that are too weak to undergo a surgical intervention and are unfit for a standard EVAR (EndoVascular Aneurysm Repair) which is a minimally invasive treatment with stent graft. The aortic endoprostheses as described herein are regarded as a promising alternative as they provide a custom made and personalized endoprosthesis that can be deployed with minimal invasiveness.

The vascular endoprostheses as described herein are customized or personalized endoprostheses, more specifically the aortic endoprosthesis is adapted to a patient's vessel anatomy. Thus, provided herein are methods for manufacturing an aortic endoprosthesis specifically fitting a patient's aorta anatomy. Custom or personalized endoprostheses may reduce the risk of suboptimal intervention results compared to standard endoprostheses, especially when the aorta anatomy has a high rate of curvature and/or a non-uniform diameter, as is the case with the aorta due to vicinity of the aortic valve, the branching of the head-and-neck vessels and the aortic arch connecting the ascending aorta to the thoracic aorta through a 180° bend.

In particular embodiments the custom or personalized vascular (e.g. aortic) endoprostheses as described herein have a shape and size, or comprise a part having a shape and size which are complementary to the shape and size of the corresponding patient's vessel (e.g. aorta) or part thereof. The patient may be a human or animal patient. In particular embodiments the custom or personalized vascular endoprostheses as described herein comprise at least one personalized region, corresponding to the patient's anatomy or multiple customized or personalized regions connected through generic regions that are not customized or personalized. For instance, the proximal and distal regions of the body structure of the aortic endoprostheses as described herein may be customized or personalized while central part of the body structure can have a generic form. This is of specific interest when using the personalized aortic endoprostheses as described herein for treating a condition of the aorta such as an aortic aneurysm or aortic dissection. For use in these embodiments, the customized or personalized regions of the aortic endoprosthesis may be positioned outside the diseased part of the aorta and the part of the aortic endoprosthesis bridging the diseased part of the aorta may be a generic lumen or a lumen corresponding to the form of the artery that would be envisioned upon repair of the artery.

As detailed above, the methods disclosed herein generally rely on information relating to the patient's vascular anatomy. This type of information is typically obtained through known medical imaging techniques. The term "medical imaging" as used herein refers to techniques and processes used to create images of the human or animal body (or parts and function thereof), typically for clinical purposes (medical procedures seeking to reveal, diagnose or examine disease) or medical science (including the study of normal anatomy and physiology). The imaging information can be obtained using any type of imaging apparatus or imaging technique which allows imaging or scanning the patient's aorta in an accurate manner. These may include equipment such as cameras and scanners for industrial, household or medical use. In particular embodiments the imaging techniques and appliances used are typical medical imaging tools such as, but not limited to computer tomography (CT) scans including for instance multi-slice CT (MSCT) scans, magnetic resonance imaging (MRI) scans, ultrasound, 3D ultrasound, Positron emission tomography (PET) scans, Single-photon emission computed tomography (SPECT) scans or other imaging modalities. A summary of medical imaging has been described in "Fundamentals of Medical imaging", by P. Suetens, Cambridge University Press, 2002.

Methods are provided herein for manufacturing a vascular endoprosthesis fitting at least part of a patient's vessel anatomy, which comprise the step of designing a 3D model of a vascular endoprosthesis, based on a 3D image of the patient's vessel anatomy or part thereof. More particularly, methods are provided herein for manufacturing an aortic endoprosthesis fitting at least part of a patient's aorta anatomy, which comprise the step of designing a 3D model of an aortic endoprosthesis, based on a 3D image of the patient's aorta anatomy or part thereof. Based on the 3D image of the patient's aorta anatomy, a 3D model of the patient's aorta anatomy or part thereof is designed. The 3D model can be obtained directly from this 3D image, for example obtained via the Mimics™ or 3-Matic™ computer program as provided by Materialise N.V., Leuven, Belgium.

In particular embodiments, methods are provided for manufacturing a personalized aortic endoprosthesis fitting at least part of a patient's aorta anatomy, comprising the steps of: providing a 3D image of the patient's aorta anatomy or part thereof; and designing a 3D model of a personalized aortic endoprosthesis based thereon.

In particular embodiments of the methods as provided herein optionally provide designing a 3D model of the patient's corrected aorta anatomy or part thereof. Small modifications can be made to the 3D image or 3D model to make a corrected 3D model. For example, certain narrowings of the aorta may be widened, such that the 3D image corresponds to a desired optimal aorta anatomy or the diseased part of the aorta anatomy may be corrected to obtain a corrected model of the aorta that is suitable for resulting in the optimal healing of the aorta anatomy. In particular embodiments, the size of the 3D model is enlarged or reduced locally, in function of the local pressure which needs to be provided by the endoprosthesis.

On the basis of the 3D model or the corrected 3D model of the aorta anatomy a 3D model of a customized or personalized aortic endoprosthesis can be designed. The customized or personalized aortic endoprosthesis is designed such that it fits to at least part of the patient's (optionally corrected) aorta anatomy and typically comprises one or more regions that are patient-specific. More particularly the customized or personalized aortic endoprosthesis typically comprises at least 2, 3, 4 or more regions that are patient-specific. In particular embodiments, the patient-specific regions of the aortic endoprosthesis are typically positioned onto or near the distal or proximal regions of the endoprosthesis or onto or near branching of the head-and-neck vessels.

In particular embodiments, methods are provided for manufacturing a personalized aortic endoprosthesis fitting at least part of a patient's aorta anatomy, comprising the steps of: providing a 3D image of the patient's aorta anatomy or part thereof; designing a 3D model of the patient's aorta anatomy or part thereof; and designing a 3D model of an aortic endoprosthesis fitting at least part of the patient's (corrected) aorta anatomy;

On the basis of the 3D model of the customized or personalized aortic endoprosthesis a 2D structure is made. In particular embodiments, the 3D model is transposed or projected onto a 2D surface thereby generating a 2D pattern which corresponds to the 3D model. The transposition from 3D to 2D is for instance performed by unwrapping the shell of the 3D model and projecting the unwrapped image onto a 2D surface or through the unrolling of the 3D model onto a 2D surface. Also other unfolding techniques such as a U-V parametrized unfolding can be used to obtain a 2D unfolded representation. In a particular embodiment the unfolded representation includes information relating to the position of the rigid rings and/or anatomical information. In particular embodiments the unfolded representation comprises features for attaching the endoprosthesis to an overlapping structure through gluing or sewing, or to remove potential holes or leakage in the 3D folded stage.

The 2D pattern is subsequently manufactured, thereby providing a 2D endoprosthesis structure. The manufacturing of the 2D structure may occur using methods typically known in the art and depending on the materials that are used. In particular embodiments the 2D structure is made from a woven or polymeric material and manufactured by cutting the 2D pattern out of a sheet of the woven or polymeric material.

In particular embodiments, it is envisioned that the 3D model may only be unfoldable in several parts (i.e. not in one part). The multiple 2D structures then need to be assembled (sewn, glued or attached by other means).

The woven or polymeric material as used in the endoprosthesis as described herein may be adjusted to achieve particular physical properties. For example, the parts of the 2D endoprosthesis structure onto which rigid rings or crowns will be attached may be rendered more stiff by taking away some of the material requiring it to be stretched into position. Similarly, particular features may be provided to allow attachment of multiple 2D structures to each other (e.g. overlap regions). In further particular embodiments, local holes may be provided or a circumferential groove or structure for attachment of the rings. Accordingly, the 2D pattern may still be adapted and features added to it. Alternatively, the 2D structure is made through additive manufacturing.

In particular embodiments of the methods envisioned herein the 2D structure is made from a polymeric material. Typically the material is characterized by being flexible, supportive, capable of expansion, and/or biocompatible. Typical materials used as polymeric material are chosen from polytetrafluoroethylene (PTFE), polyethylene (PE), polyethylene terephtalate, silicone, polyglycolic acid, polylactic acid and/or polyurethane or other woven fabric materials or polymers.

The 2D endoprosthesis structure may be created based on the virtually corrected vessel structure. This correction can be based on average population data and as such fit an average vessel portion through the healthy anatomy parts and as such close e.g. a sick gap. An alternative correction method would be to use computer simulation in order to establish optimal strength or flow based parameters. Another alternative method can be to perform a tangent fit to bridge the diseased anatomy.

The 3D model of the aortic endoprosthesis is provided as described above, can also be used to generate a mold for the manufacture of the endoprosthesis, more particularly a mold which can be used as a support, for wrapping the 2D structure of the endoprosthesis into a 3D device.

In particular embodiments, the 3D model of the aortic endoprosthesis is used to design and manufacture a crushable mold or a flexible mold. The mold can in particular embodiments also be manufactured based on a 3D image of the aortic endoprosthesis. In these embodiments, the mold for the endoprosthesis will at least partially correspond to a 3D model of the patient's aorta such that the wrapping the 2D endoprosthesis structure tightly thereon, will result in a 3D endoprosthesis which corresponds at least in part to the anatomy of the patient's aorta. The terms "mold" and "mandrel" are used interchangeably herein and refer to three dimensional objects of which the shape and surface is made specifically such that it can be used to ensure a desired shape and surface in an object manufactured thereon.

The terms "flexible" mold or support as used herein refers to a mold or support that is not rigid. More particularly the mold or support can be flexible in that it can be increased in size by the application of pressure e.g. by providing air or liquid pressure. This can be achieved by the use of flexible polymers. After printing, the flexible mold or support is made more rigid by adding pressure. After the endoprosthesis is made on the mold or support, the pressure is removed such that the flexible mold or support can be removed from the endoprosthesis. A flexible mold can be patient-specific and optionally be made based on a 3D model of the endoprosthesis. However, the use of flexible supports are also envisioned in this context, i.e. support structures such as balloons which can provide sufficient support for assembling the 2D endoprosthesis structure into the 3D endoprosthesis.

The terms "crushable" mold or support as used herein refers to a mold or support that is characterized by being able to be broken down in a controlled manner into discrete pieces. After an object is made around a crushable mold or support, the mold or support itself can be broken down by applying pressure thereto and the mold pieces can be removed without having to interfere with the object made. In particular, the crushable mold or support is an ordered mold or support comprising strong pieces linked through weaker grooves (strong and weak being determined as able to withstand the envisioned pressure). As a result, upon pressurizing the crushable mold or support, it will crumble into predetermined pieces of similar size and shape. This is in contrast to non-crushable molds or supports which may also break when subjected to pressure, but will in most cases require much higher pressures and in addition do so in an uncontrolled, unexpected and often undesired manner. In particular, the crushable mold or support is structure which exhibits controlled fracturing along the weaker grooves or seams resulting into smaller pieces. In particular embodiments, the envisioned pieces of a vascular endoprosthesis mold as envisioned herein are equal to or preferably smaller than the diameter of the mold corresponding to the inner diameter of the corresponding vascular endoprosthesis, such that the mold can be broken within the vascular endoprosthesis and the pieces can be removed through the lumen of the endoprosthesis.

These methods allow the manufacturing of complex objects with complex structures on a mold or support without having to disassemble and reassemble these objects to remove the mold. In the methods envisioned herein, as the mold or support of the endoprosthesis is envisioned to be flexible or crushable, it can be removed without affecting the integrity of the endoprosthesis assembled thereon.

As described above, the structure for supporting the 2D structure during its assembly to a 3D endoprosthesis may, but need not be patient-specific. Thus, in particular embodiments, it is envisioned that use is made of a crushable support, which is a standard support structure which can be broken down in a controlled way.

Alternatively, in particular embodiments, where the 3D model of the endoprosthesis is envisioned for use both for the provision of the 2D structure of the endoprosthesis and for the provision of the mold for supporting the 2D structure, it is envisioned that the step of providing the 3D model of the aortic endoprosthesis may in some embodiments include an optional step of adapting the 3D model of the aortic endoprosthesis to include additional structural features. Such structural features may be specific for the provision of the 2D structure of the endoprosthesis or for the provision of the mold. In particular embodiments, different adapted 3D models are provided for each of these applications. Examples of additional structural features include features such as for instance features conform to ring structures (as will be described herein below) that are to be attached to the endoprosthesis and/or attachment structures for attaching the ring structures to the endoprosthesis. Providing groove structures on the 3D model of the endoprosthesis corresponding to the envisioned position of the ring structures (as will be detailed below) may ensure that the ring structures will be embedded within the endoprosthesis and do no protrude significantly from the surface of the endoprosthesis. In particular embodiments, the positions of the rings is specifically selected to be positioned in the landing zones and/or removed from the head and neck vessels or from weakened or deformed anatomy.

In particular embodiments, it is envisioned that the endoprosthesis may be provided with particular features related to its use, such as but not limited to features for attachment, and/or deployment elements. Accordingly, in certain embodiments, the 3D model of the endoprosthesis may be provided with features (such as for example recesses) for accommodating deployment elements or for attachment of the ring structures of the endoprosthesis.

Similarly it is envisioned that in particular embodiments, in the design of the mold based on the 3D model of the endoprosthesis, particular features are provided on the model for this purpose. For instance, in particular embodiments, the 3D model of the endoprosthesis is used for the design of a crushable mold. The model is meshed so as to provide a tiled structure, more particularly tile pieces and spacings between the tile pieces thereby providing features allowing the mold to be broken down in a controlled manner. Examples of envisioned crushable molds will be discussed in more detail below.

In the methods for the manufacture of an endoprosthesis envisioned herein, the 2D endoprosthesis structure is assembled back into a 3D shape on the (crushable or flexible) mold. This is typically done by wrapping the 2D structure around the mold. The 2D structure is folded onto the mold. Either before or after the wrapping of the 2D structure, rigid rings or crowns are positioned onto the mold. The individual size and circumferential length or the rings or crowns can optionally be established from 3D images. The rings are attached to the wrapped 2D structure, i.e. the endoprosthesis scaffold, optionally making use of specific attachment features provided on the 2D structure during its manufacture as described above. In particular embodiments, the rings or crowns are sewn to the endoprosthesis scaffold. The rigid rings may thus be positioned on the inside or the outside of the endoprosthesis.

After assembling the mold is removed and the structure that was wrapped around the mold forms the personalized aortic endoprosthesis as described herein.

In the methods envisioned herein making use of a crushable mold, the mold is removed from the endoprosthesis by mechanically breaking the mandrel by applying (external) mechanical force. In particular embodiments, as will be detailed below, the mold is made of tile pieces interlinked by weakened seams, such that the mandrel can be broken in a controlled way, and that the individual tile pieces can be removed easily from the endoprosthesis. In further embodiments making use of flexible mold, the mold is removed by reducing the size and/or rigidity of the mold, e.g. by removing the pressure thereon. In both embodiments, endoprosthesis removal does not involve the use of hazardous acids as required for the method of U.S. Patent Application No. 2005/096729.

In particular embodiments the methods as described herein provide that the assembling of the 2D endoprosthesis structure around the mold comprises attaching one or more rigid rings onto the 2D structure around the mold. Ring structures suitable for use in the context of the endoprostheses are known in the art, such as, for instance but not limited to from US 2009/0163998. The "rigid rings" as referred to herein in fact correspond to structures having a shape which can, in most cases be positioned circumferentially around the mold and/or 3D endoprosthesis, and are thus essentially circular. However, as detailed herein, where the endoprosthesis does not have a circular cross-section, the rigid ring will be semi-circular or extend to form only part of a circle. The shape of the rigid rings is however not necessarily straight but is more often jagged or curved resulting in a more crown-like shape. The rigid rings, while envisioned to be more rigid in structure than the endoprosthesis material, in particular embodiments, can be bent to match the patient specific anatomy. As used herein, the term rigid is employed herein to indicate the limited flexibility of the structure of the rings or crowns. This rigidity allows them to ensure the flow through of the device. However, it will be understood to the skilled person that in particular embodiments, the rings or crowns may be ensured that they are nevertheless expandable, e.g. in the case of deployable devices, while maintaining their general structure.

Such rigid rings, in particular embodiments also referred to as crowns, which typically serve to maintain the 2D endoprosthesis structure in its 3D shape are typically made from a material such as a metal, a ceramic material or carbon material. More particularly, typical materials that can be used for the rigid rings as described herein are chosen from metals or metal alloys such as Nitinol, stainless steel, titanium, platinum, gold, cobalt-chromium alloy, tantalum alloy, a carbon material such as pyrolitic carbon or a ceramic or glass material known in the art.

In a particular embodiment the rigid rings or crowns are made in Nitinol (or another self-expanding material). Nitinol rings are typically used when the personalized aortic endoprosthesis as described herein is self-deployable.

The deployment of the personalized aortic endoprosthesis as described herein may also be performed by (a multistage) balloon expansion as described herein. The rigid rings of the balloon expanding devices are usually made of Co—CR (Cobalt-Chromium), Stainless Steel, platinum, or other materials known in the art. In a particular embodiment the rigid rings used to ensure rigidity and/or maintain the structure of the endoprosthesis are patient-specific or comprise patient-specific features.

Typically, the rigid rings will follow the circumference of the endoprosthesis. In particular embodiments however, some of the rigid rings do not form a complete 360° circle, more particularly in those parts of the endoprosthesis comprising openings to allow passage for vessels, such as head and neck vessels in the aorta. For the rigid rings located at or near the head and neck vessels their circumferential length is estimated from local vessel perimeter and local size of the head and neck vessels or other geometrical, structural or tissue-related parameters in order to not obstruct those latter vessels. In particular embodiments the rings or crowns are isolated structures. However, the different rings or crowns may also be interconnected.

The attachment of the rigid rings onto the 2D structure can optionally be ensured using any one of a number of generally available techniques including, but not limited to, stitching or alternative attachment forms.

In general, the materials used in vascular endoprostheses (i.e. the 2D endoprosthesis structure material and rings or attachment structures therefore) are typically composed of biocompatible materials, as materials that are not biocompatible can cause one of any number of complications. Typically the vascular endoprostheses as described herein does not cause a reaction in the human body.

In particular embodiments, methods are provided for manufacturing a personalized aortic endoprosthesis fitting at least part of a patient's aorta anatomy, comprising the steps of: providing a 3D image of the patient's aorta anatomy or part thereof; designing a 3D model of the patient's aorta anatomy or part thereof; designing a 3D model of an aortic endoprosthesis fitting at least part of the patient's (corrected) aorta anatomy; transposing the 3D model to a 2D pattern; manufacturing from the 2D pattern a 2D structure; and optionally designing an adapted 3D model of the aortic endoprosthesis.

As detailed above, it is envisioned that, in light of the use of the rings and attachment structures described below, the 3D model of the endoprosthesis used may in particular embodiments comprise features such as grooves conform to one or more rigid rings and/or the attachment structures for attaching the rigid rings onto the 2D structure. The grooves allow easier and optimized positioning of the rings. In this way the rings can be positioned based on the 3D images in the patient-specific features or away from the head and neck vessels or weakened or deformed aorta anatomy. Thus in particular embodiments, the location of the grooves is selected based on the location of healthy and diseased tissue, local anatomy and expected tissue properties which can be derived from the 3D image. Additionally or alternatively, in particular embodiments the 3D model of the aortic endoprosthesis fitting at least part of the patient's (corrected) aorta anatomy comprises features such as those selected from holes, stable landing zones, defined zones for rigid rings and/or areas allowing the delivery of active agents. More particularly, in particular embodiments the introduction of holes into the 3D model of the aortic endoprosthesis may be required to ensure that blood flow towards branching vessels is maintained. Also particularly the stable landing zones may be introduced at this stage of the process, wherein the "stable landing zones" refer to regions of the aortic endoprosthesis that are patient-specific. In particular embodiments the stable landing zones are selected anatomical regions which, based on information regarding the variation in function of time of the anatomy of the lumen in the anatomical area of interest for placing the vascular endoprosthesis, as anatomical regions within this anatomical area showing greater stability in time. This will ensure that the endoprosthesis can be nested stably against a specific region of the lumen wall of the patient, and has an increased chance of being maintained in this position.

In particular as detailed above, defined zones may be added that upon assembly correspond to the position of rigid rings that are attached to the 2D structure. These zones may also be determined by the landing zones determined above.

Finally, it is also envisioned that in the design of the 3D model of the endoprosthesis specific features are added such as features or structures that can be used for the delivery of active agents and medicines into the blood flow.

In particular embodiments, the methods for manufacturing an endoprosthesis as envisioned herein further comprise the step of coating the endoprosthesis. This coating can be ensured before or after removal of the mold, but is typically envisioned after the mold has been removed. In particular embodiments, the coating is an (inert) coating selected from the group consisting of polysulfone, silicone rubber, polyurethane, synthetic glycocalix, amorphous silicon carbide, diamond-like carbon, magnesium phosphate, magnesium oxide, or mixtures thereof.

In further particular embodiments, the methods for manufacturing an endoprosthesis as envisioned herein comprise the step of loading the endoprosthesis with a substance. This is particularly envisioned for those embodiments where the endoprosthesis is provided with features suitable for administration of a composition during use, as will be detailed below. In particular embodiments, the methods for manufacturing an endoprosthesis as envisioned herein may comprise the step of grafting biological material onto the endoprosthesis. Suitable methods for carrying out grafting on implantable devices are known in the art.

In particular embodiments the methods as described herein comprise manufacturing the mold by additive manufacturing. In particular, additive manufacturing refers to techniques such as stereolithography, selective laser sintering, selective laser melting and/or fused deposition modeling.

The application also provides personalized vascular endoprostheses, such as those obtainable by the methods as described herein.

In particular embodiments, the personalized vascular endoprostheses comprise a hollow tubular body comprising a proximal end and a distal end, wherein the hollow tubular body provides a central longitudinal axis, the body further comprising a stent scaffold made from a polymeric material and one or more rigid ring structures encircling and attached to the stent scaffold, wherein the outer surface of the stent scaffold comprises at least one area complementary to at least part of a patient's aorta anatomy.

Thus, the endoprosthesis is typically made up of the stent scaffold and rigid ring or crown structures attached thereto. In particular embodiments, the material used for the endoprosthesis can be adjusted to achieve specific properties in specific areas of the endoprosthesis. For instance, it is envisioned that the rigidity of the material can be adjusted to provide regions of increased stiffness to allow attachment of the rigid rings thereto. Thus, in particular embodiments, the scaffold material will vary in rigidity depending on the areas of the endoprosthesis.

More particularly, the endoprostheses may comprise at least one non-circular cross-section along the length of the stent's longitudinal axis. Accordingly, in particular embodiments, the endoprostheses comprise one or more features to better adapt the tubular body to the patient's anatomy including, but not limited to apertures, tapering, beveling, non-circular cross-sections, flaring or branching of the body of the endoprosthesis.

In particular embodiments the endoprosthesis as envisioned herein is an aortic endoprosthesis and comprises one or more openings for the connection with head and neck vessels, which can be optimized and made patient in a patient specific nature. In particular embodiments, the opening extends over the entire section of the aortic arch going into the head and neck vessels.

In particular embodiments, endoprostheses are envisioned wherein the part which has a non-circular cross-section is nevertheless provided with a rigid structure, which extends across the endoprosthesis wall and thus is also non-circular in that part. The provision of rigid structures nevertheless can ensure additional support for the endoprosthesis in this part.

In particular embodiments the personalized aortic endoprostheses comprises a region complementary to at least part of the ascending aorta, the aortic arch and/or the thoracic aorta. In further particular embodiments, this "personalized region" is a region corresponding to a non-diseased region of the aorta.

In particular embodiments the custom or personalized aortic endoprostheses as described herein are either self-deployable or balloon deployable. The endoprosthesis as envisioned herein may be self-expanding or balloon expandable. A self-expanding endoprosthesis has the ability to revert readily from a reduced profile configuration to a larger profile configuration in the absence of a restraint upon the device that maintains the device in the reduced profile configuration. Balloon expandable refers to a device that comprises a reduced profile configuration and an expanded profile configuration, and undergoes a transition from the reduced configuration to the expanded configuration via the outward radial force of a balloon expanded by any suitable inflation medium.

The deployment is in particularly performed via a typical and commonly used catheter procedure. Such a procedure typically comprises the steps of puncturing the vessel (typically in a femoral artery in the groin), introducing a sheath, introducing a guidewire into the vessel and bringing the guidewire beyond the position of deployment of the device (the latter is typically done under fluoro guidance using for instance a pig tail catheter to inject contrast into the vessel) and introducing a catheter with the device mounted to it. Ideally, the device should have radio-opaque markers indicating the key locations on the device: start and end of landing zone, onset and end of head-& neck vessel opening, end of prosthesis etc. The device can be positioned and expanded under fluoro guidance.

For balloon expanded devices, both one-stage expansion and multi-stage expansion are envisioned. In particular embodiments, where the endoprosthesis is an aortic endoprosthesis and comprises an opening spanning the connection with the head and neck vessels, a specific order of deployment can be envisioned, in order to limit duration of vessel blockage. More particularly it can be envisioned that, expansion takes place in the following stages: 1 ascending aorta, 2 portion with opening for head and neck vessels, and 3 distal portion to head and neck vessels.

In particular embodiments, the endoprosthesis is a self-expanding device. In this case expansion occurs by the device being forced out of the catheter and seeking its natural state of expansion. In case of an aortic endoprosthesis which comprises an opening spanning the connection with the head and neck vessels and both a portion proximal (i.e. ascending aorta) and distal thereto, the deployment will occur in a similar sequence as described above, as these sections of the device will exit the catheter in that order.

The 3-stage deployment as described above will allow for a deployment in which the device will already allow blood to flow to the body again after phase 1 (i.e. during phase 2). In phase 3 the descending aorta will be temporarily occluded again. Ideally, in this embodiment the opening(s) in the endoprosthesis for the head and neck vessels are sufficiently large while maintaining a sufficient amount of external force to conform to the lower part of the aortic arch wall.

Thus, in particular embodiments, the endoprosthesis comprises one or more openings for the head and neck vessels which are sufficiently large, while maintaining a section supporting the lower arch of the aortic arch wall. In further particular embodiments, this support is provided by the ring structures in the device.

In particular embodiments, the endoprosthesis may be provided with hook-like elements or other elements which facilitate deployment.

The length and diameter of the endoprosthesis as envisioned herein depends on the anatomy of the aorta into which it is to be deployed. For example, a thoracic endoprosthesis typically has a length between 10 and 20 cm and a diameter between 25 and 40 mm.

In particular embodiments the endoprosthesis may be partially covered by a graft material such as but not limited to an engineered, animal, human or tissue. In further particular embodiments, the endoprosthesis further comprises a heart valve or comprises an engineered heart valve (i.e. of human or animal material) integrated into the structure. In particular embodiments, personalized aortic endoprosthesis as described herein is characterized in that the personalized aortic endoprosthesis fits at least partially with the ascending aorta, the aortic arch and/or the thoracic aorta.

The ascending aorta is the portion of the aorta commencing at the upper part of the base of the left ventricle, on a level with the lower border of the third costal cartilage behind the left half of the sternum; it passes obliquely upward, forward, and to the right, in the direction of the heart's axis, as high as the upper border of the second right costal cartilage, describing a slight curve in its course.

The aortic arch or the transverse aortic arch refers to the part of the aorta that begins at the level of the upper border of the second sternocostal articulation of the right side, and runs at first upward, backward, and to the left in front of the trachea; it is then directed backward on the left side of the trachea and finally passes downward on the left side of the body of the fourth thoracic vertebra, at the lower border of which it becomes continuous with the descending aorta. It thus forms two curvatures: one with its convexity upward, the other with its convexity forward and to the left. Its upper border is usually about 2.5 cm. below the superior border to the manubrium sterni.

The thoracic aorta is contained in the posterior mediastinal cavity and begins at the lower border of the fourth thoracic vertebra where it is continuous with the aortic arch, and ends in front of the lower border of the twelfth thoracic vertebra, at the aortic hiatus in the diaphragm where it becomes the abdominal aorta.

As detailed above, the methods described herein make use of a crushable mold or support. Where a crushable mold is used, the mold is typically made based on the 3D model of the endoprosthesis. Particular embodiments of the crushable objects including molds are provided in patent application EP 11 184365.2 (which is incorporated herein by reference). This will be detailed herein for the provision of a crushable mold. It will be understood however, that non-patient-specific objects can be made "crushable" in a similar way, starting from a 3D image of the object.

Typically, the crushable aspect of the mold is obtained by dividing the 3D model of the aortic endoprosthesis into two or more sub-domains, which are herein referred to as "tile pieces" or "tiles". This process is referred to as meshing. The object of the meshing process is to determine how the mold can be broken, i.e. which pieces will be formed. More particularly, the object is to ensure that the mold is broken into two or more fragments in a controlled way, such that the endoprosthesis can be removed from the mold. Therefore, the 3D image or model is meshed at least in those areas where the corresponding mold will need to be broken e.g.

where it is expected to be difficult to remove from the endoprosthesis. In certain embodiments, the tile pieces are similar pieces, preferably pieces with a similar size, even more preferably pieces with a similar size and shape. However, as will be detailed below, the pieces may differ in size and shape.

According to a particular embodiment, the meshing is used during the manufacturing process to ensure the production of the mold in pieces which are separated by spacings. Indeed, as will be detailed below, the mold is manufactured such that at the joints of the tile pieces the strength of the mold is reduced compared to the tile pieces themselves. This ensures that, when pressure is put on the mold, it breaks apart at the joints.

Accordingly, methods are provided for manufacturing the mold whereby the mold is provided as a plurality of pieces or tiles, which are connected through seams, which seams can be broken when the mold is subjected to a manual pressure. More particularly, the methods as described herein comprise the step of meshing the mold (or an image or model thereof), so as to determine the location of the seams forming the pieces making up the mold or mold part. In particular embodiments, the meshing is performed without changing the outline of the model. For example, this can be understood as removing one or more thin slices from the image, such that the remaining tile pieces are separated by spacings at the original location of the removed slices.

Accordingly, in particular embodiments, the methods as provided herein involve meshing the image or the model of the mold so as to divide it into two or more tile pieces and spacings between the tile pieces, preferably without changing the relative position of the tile pieces and/or the outline of the image.

As indicated above, in particular embodiments, the individual tiles have the same shape and size. However, the individual tile pieces may vary in shape or form according to the required specifications of the mold and/or endoprosthesis. The tile pieces may form a structured or unstructured mesh. A structured mesh is characterized by regular connectivity that can be expressed as a two or three dimensional array. An unstructured mesh is characterized by irregular connectivity. In preferred embodiments, the tile pieces form a structured mesh.

In certain embodiments, the tile pieces are essentially geometric pieces such as triangles, squares, rectangles, pentagons and/or hexagons. Thereby, the tile pieces ensure a tiled structure of the mold. Also combinations of these shapes and/or other suitable geometries may be considered. In particular embodiments, the tile pieces are triangular, square, rectangular, pentagonal and/or hexagonal prisms. Typically, the overall shape and size of the tile is determined by the desired requirements and impact of breaking the mold (i.e. the amount of pressure to be applied and the resulting pieces to be generated).

It is envisioned that in particular embodiments the tile pieces at one or more surfaces of the mold have a different shape than the tile pieces which are more removed from the border of the mold. Therefore, in particular embodiments, at least 20, 30, 40, 50, 60, 70, 80 or 90 percent of the tile pieces have a similar or identical shape.

Additionally or alternatively, it is envisioned that the surface of the tiles making up the outer surface of the mold for the endoprosthesis is not geometrical. Indeed, typically the interconnecting sides of the tiles will be have a geometrical or regular shape, while the surface of the tile which is intended to contact the endoprosthesis is not.

The number of tile pieces provided in the image or model of the mold during the meshing process depends on various factors such as the size and shape of the mold and/or the endoprosthesis to be made. In certain embodiments, the model is provided with three, five, ten, twenty, fifty, hundred or more tile pieces. In particular embodiments, the meshing ensures the provision of at least 5 tile pieces in the mold, more particularly at least ten tile pieces in the mold, more particularly at least 20 pieces.

In certain embodiments, the tile pieces have a size between 2 mm$^2$ and 10 mm$^2$. In particular embodiments, the mold surface comprises between 0.25 and 25 tile pieces per cm$^2$. However by using state of the art technologies such as laser micro sintering, the resolution of the manufactured molds can be reduced below the limits commercial SLS devices, providing resolution of less than 30 μm. Accordingly, in certain embodiments, the tile pieces may have a typical surface dimension below 2 mm$^2$ and typically ranging from 250 μm$^2$ to 4 cm$^2$.

In most embodiments it is envisioned that all or most of the pieces have a similar size, more particularly sizes which differ at most by 5-10%. In particular embodiments, the meshing step ensures the provision of at least ten pieces whereby all or most of the pieces have a similar size, more particularly sizes which differ at most by 5-10%. Typically, while in certain embodiments, only part of the mold may be meshed, the meshed area will comprise of at least ten pieces whereby all of the pieces have a similar size.

As detailed above, the meshing step provides tiles which are connected (or separated) by spacings or seams. In particular embodiments, the spacings or seams between adjacent tile pieces have planar geometry and have a uniform width. Consequently, in particular embodiments, the neighboring surfaces of two adjacent pieces or tiles have a planar geometry.

However, the spacings or seams and neighboring surfaces may also have other shapes and/or may have a non-uniform width. In particular embodiments, the adjoining surfaces of the tiles have a curved, jagged, serrated, corrugated or notched shape or geometry. In particular embodiments, the seams or spacings have a uniform width. An important advantage of non-planar adjoining surfaces of the tiles is their enlarged area compared to when the adjoining surfaces are planar. This allows engineering of the seams to a certain intended breaking force. Indeed, the seam surface strongly influences the seam strength. Additionally or alternatively, these shapes may provide seams with different strength in different directions. Furthermore, gaps with a non-uniform width may provide tailored strong and weak areas within the seams.

Thus, by determining the number, shape and size of the tiles in the mold and the width of the seams between them, the breaking of the mold upon applying pressure is controlled. Typically the desired strength of the seams is such that it is breakable by hand and typically ranges between 1 to 100 N and preferably between 1 and 50 N.

The mold used in the methods envisioned herein is typically made via additive manufacturing. Typically, an AM apparatus builds objects on a layer-by-layer basis.

Additive Manufacturing can be defined as a group of techniques used to fabricate a tangible mold of an object typically using three-dimensional (3-D) computer aided design (CAD) data of the object. Currently, a multitude of Additive Manufacturing techniques is available, including Selective Laser Sintering, stereolithography, Fused Deposition Modeling, foil-based techniques, etc.

Selective laser sintering (SLS) and selective laser melting use a high power laser or another focused heat source to sinter or weld small particles of plastic, metal, or ceramic powders into a mass representing the 3-dimensional object to be formed. Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680. Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

Thus particular embodiments comprise manufacturing the mold by additive manufacturing, thereby providing a mold comprising two or more tile pieces and spacings or seams between the tile pieces which have a reduced strength compared to the tiles. In particular embodiments, the tile pieces are manufactured according to the meshed model, i.e. such that they are set in a position relative to each other corresponding to their position in the model, and preferably without changing the outline of the mold.

In particular embodiments, the mold is manufactured by SLS. Using SLS, the mold can be manufactured by sintering only the tile pieces. Provided the seam is kept sufficiently narrow, the tiles remain interlinked at the seams but the strength of the mold at the seams is reduced compared to the strength of the tile pieces. The thermal energy provided by a laser onto the powder material will also cause some sintering of the powder surrounding the individual tile pieces so that they remain connected. As however, less material is sintered, the strength of the seams will be weaker than the strength of the tile pieces.

Thus, even though the laser of the SLS device is not specifically applied to the particles or powder at the locations corresponding to the spacings or seams in the mold, the particles or powder at these locations still are sintered, albeit less than the sintered particles or powder forming the tile pieces of the mold.

In alternative embodiments, the laser is also applied to the particles or powder at the locations corresponding to the spacings between the tile pieces, but the (laser) power delivered to the particles or powder at the locations corresponding to the spacings or seams is lower than the power delivered to the particles or powder at the locations corresponding to the tile pieces. This also still results in areas with different degrees of sintering of the powder (i.e. the tile pieces and the seams) and thus different strength, but provides a better control of the seam strength.

Thus, the mold obtained by the present method comprises two or more tile pieces which are linked by weakened seams. The weakened seams allow breaking of the mold in a controlled and predefined way, which facilitates removal of the endoprosthesis from the mold. Another advantage is that the weakened seams can be made such that they do not compromise the rigidity of the mold. Therefore, the seams do not increase the risk of mold deformation during the manufacture of the endoprosthesis.

Additive manufacturing is particularly useful for the manufacture of hollow objects. Accordingly, in certain embodiments, the mold for an endoprosthesis is hollow. This reduces the amount of material necessary to make the mold. A hollow mold is also easier to break, which facilitates removal of the endoprosthesis from the mold.

The material used to manufacture the mold or mandrel may depend on the (additive) manufacturing method used and the specifications of the endoprosthesis to be manufactured. In particular embodiments, the mandrel is made of a material which is compatible with additive manufacturing, including polymeric materials, metals, metal alloys, ceramic materials and glass. In preferred embodiments, the mold is made of polyamide, polystyrene, steel, titanium, or aluminum. The mold may also be made of a composite material, preferably glass-filled polyamide or alumide. Alumide is a blend of polyamide and aluminum powder. Typical mold (part) materials include for instance DSM Somos® series of materials 7100, 8100, 9100, 9420, 10100, 11100, 12110, 14120 and 15100 (from DSM Somos); ABSplus-P430, ABSi, ABS-ESDI, ABS-M30, ABS-M30i, PC-ABS, PC-ISO, PC, ULTEM 9085, PPSF and PPSU materials (from Stratasys); Accura Plastic, DuraForm, CastForm, Laserform and VisiJet line materials (from 3-Systems); Aluminum, CobaltChrome and Stainless Steel materials, Maranging-Steel, Nickel Alloy, Titanium, the PA line of materials, PrimeCast and PrimePart materials and Alumide and CarbonMide (from EOS GmbH).

Another embodiment provides a computer-readable medium adapted to perform the different steps of the method as described herein. More particularly, it is provided in a data processing apparatus of system which comprises means for carrying out the method as described herein, in a computer program adapted to perform the different steps of the method as provided herein carried on an electrical carrier signal or a computer program comprising software code adapted to perform the method as described herein. The data processing system or computer program as provided herein particularly refer to computer aided design and manufacturing systems and programs such as CAD/CAM systems or programs.

The present invention will be illustrated by the following non-limiting embodiments.

Examples

Figure 2:
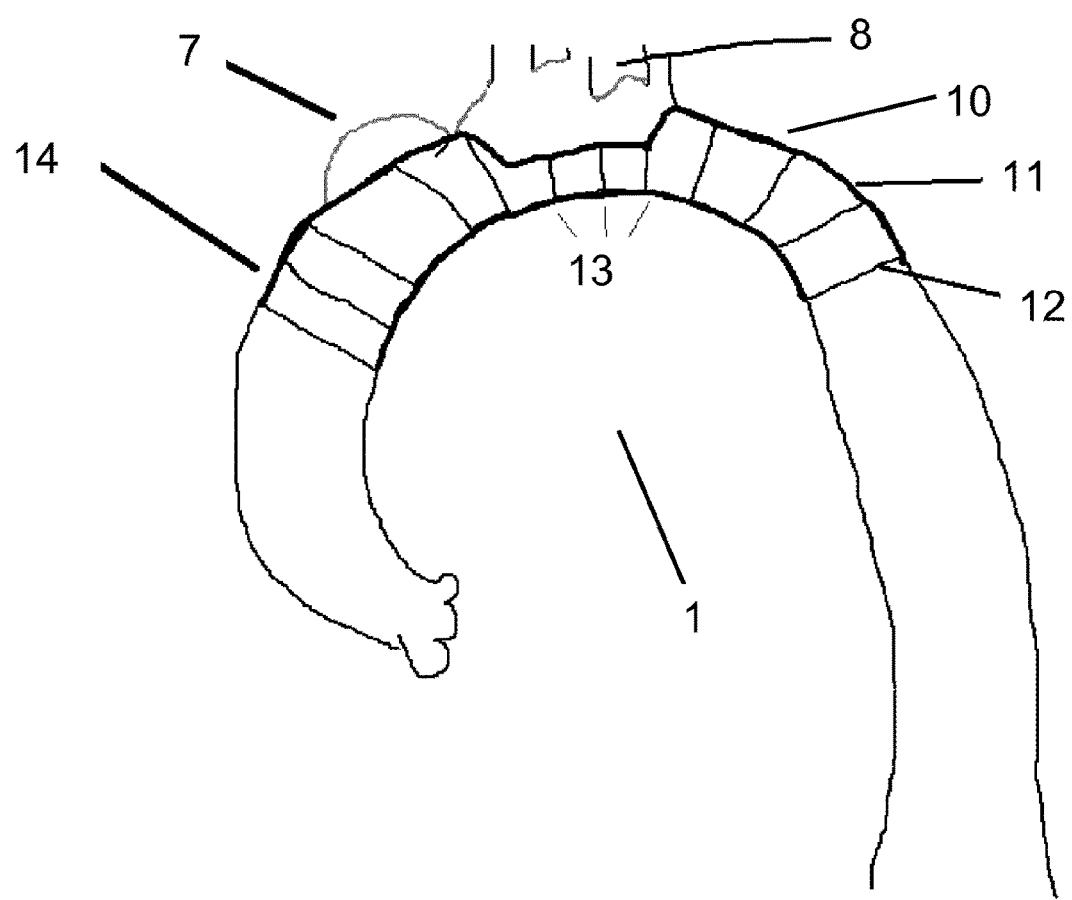
FIG. 2—Schematic representation of a diseased patient's aorta anatomy and the position of a customized aortic endoprosthesis.

FIG. 2 shows a schematic representation of a diseased aorta anatomy into which a customized aortic endoprosthesis according to a particular embodiment is provided. A normal aorta anatomy (1) as shown in FIG. 1 starts at the aortic valve (5) and comprises the ascending aorta (2), the aortic arch (3) and the thoracic aorta (4). The aortic arch comprises several branched vessels including the head and neck vessels (6). The diseased aorta anatomy as shown in FIG. 2 includes a diseased ascending aorta (7) and a diseased aortic arch (8) going into the head and neck vessels. Using a customized aortic endoprosthesis (10) as described herein, the diseased aorta can be treated in a fast and efficient manner. The endoprosthesis comprises a scaffold (11) preferably made from a polymeric or a woven fabric material and one or more rigid ring structures (12) encircling and attached to the scaffold. The endoprosthesis also comprises patient-specific features (14). According to particular embodiments the endoprosthesis may also comprise a part which forms a partial endoprosthesis (13) which only partially covers the circumference of the aorta anatomy, thereby leaving an opening for ensuring blood flow into the branched head and neck vessels.

Figure 3:
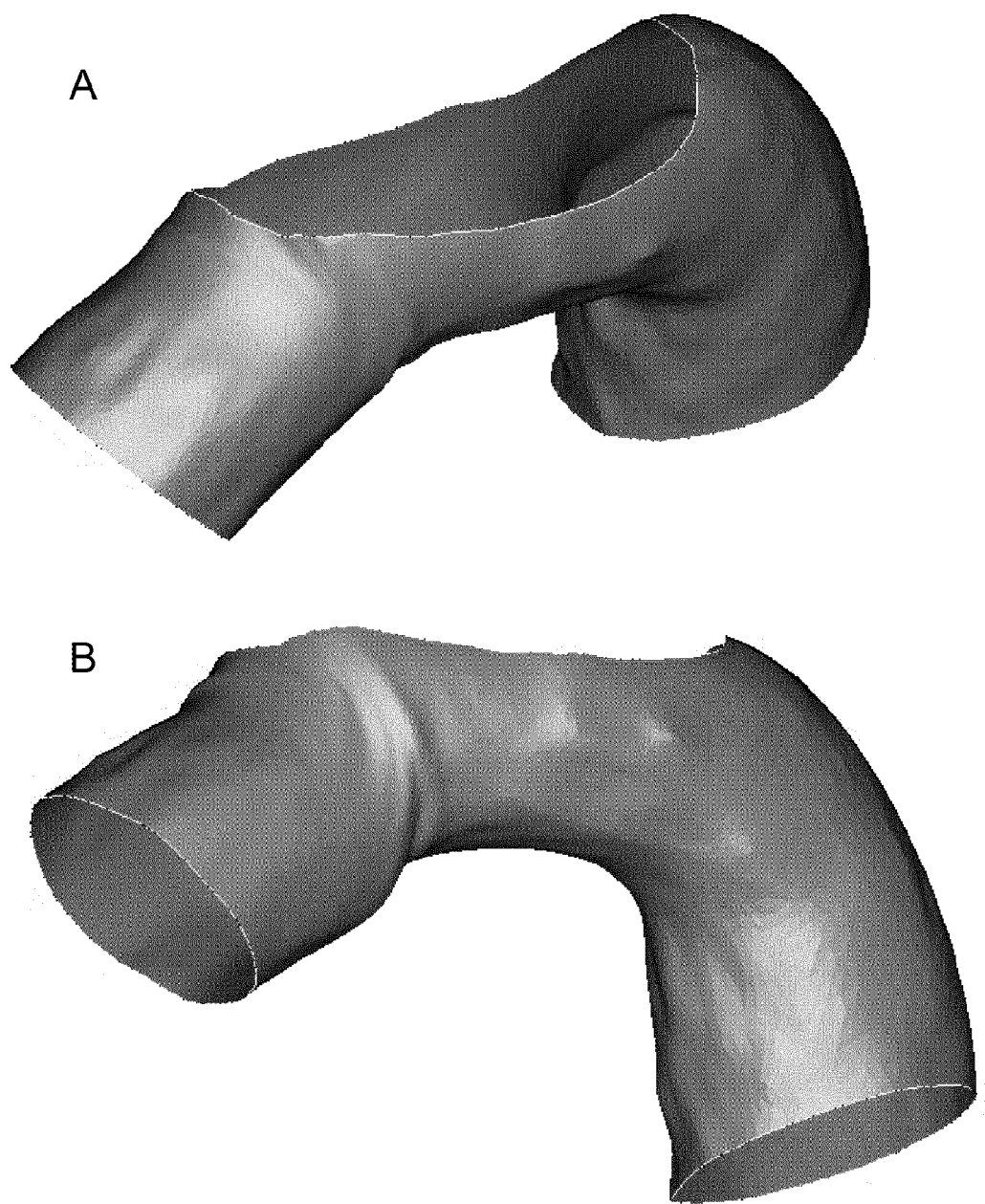

FIGS. 3A and 3B show 3D images of the customized aortic endoprosthesis as described herein.

Figure 4:
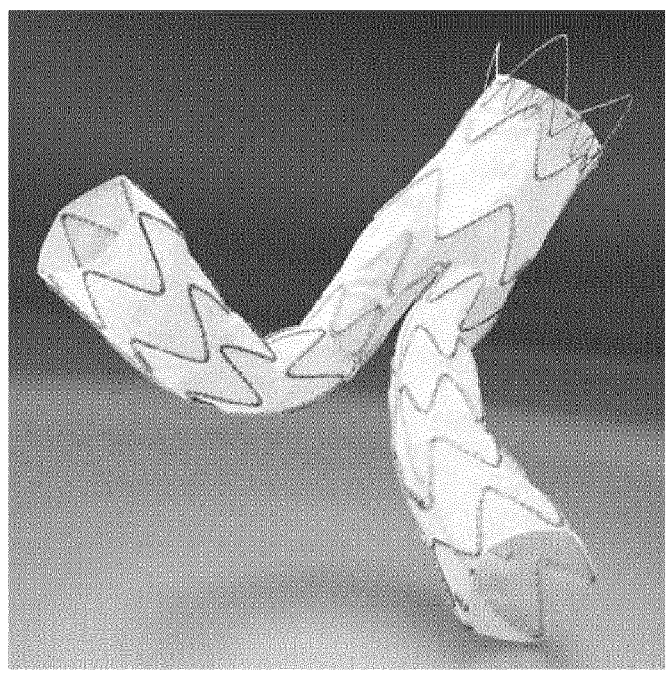
FIG. 4—example of an endoprosthesis, comprising, attached thereto, rigid rings in the form of crowns, such as those that can be used in the endoprostheses envisioned herein.

FIG. 4 shows a picture of an embodiment of suitable rigid ring or crown structures which can be used for attachment to an endoprosthesis scaffold. In the figures shown, the crowns are stitched into the endoprosthesis material.

What is claimed is:

1. A method for manufacturing a vascular endoprosthesis fitting at least part of a patient's lumen anatomy, the method comprising:
    obtaining a 3D image of a region of the patient's lumen anatomy comprising the at least part of the patient's lumen anatomy;
    obtaining a corrected 3D model of the region of the patient's lumen anatomy based on the 3D image of the region of the patient's lumen anatomy;
    designing a 3D model of the vascular endoprosthesis based on the corrected 3D model of the region of the patient's lumen anatomy;
    unfolding the 3D model of the vascular endoprosthesis to a 2D pattern of the vascular endoprosthesis;
    manufacturing a 2D endoprosthesis structure from the 2D pattern; and
    assembling the 2D endoprosthesis structure to obtain a 3D endoprosthesis corresponding to the 3D model of the vascular endoprosthesis.

2. The method of claim 1, wherein obtaining the corrected 3D model of the region of the patient's lumen anatomy comprises correcting a portion of the 3D image or a 3D model based on the 3D image corresponding to a diseased portion of the region of the patient's lumen anatomy.

3. The method of claim 1, wherein obtaining the corrected 3D model of the region of the patient's lumen anatomy comprises locally enlarging or reducing a size of a portion of the 3D image or a 3D model based on the 3D image corresponding to a portion of the region of the patient's lumen anatomy.

4. The method of claim 1, wherein obtaining the corrected 3D model of the region of the patient's lumen anatomy comprises locally correcting a portion of the 3D image or a 3D model based on the 3D image corresponding to a portion of the region of the patient's lumen anatomy based on average population data.

5. The method of claim 4, wherein correcting the portion of the 3D image or the 3D model based on the 3D image corresponding to the portion of the region of the patient's lumen anatomy based on average population data comprises fitting an average vessel portion to one or more healthy anatomy parts in the portion of the 3D image or the 3D model based on the 3D image so as to close at least one diseased part in the portion of the 3D image or the 3D model based on the 3D image.

6. The method of claim 1, wherein obtaining the corrected 3D model of the region of the patient's lumen anatomy comprises using computer simulation of at least one of strength and flow-based parameters of a portion of the region of the patient's lumen anatomy.

7. The method of claim 1, wherein obtaining the corrected 3D model of the region of the patient's lumen anatomy comprises performing a tangent fit to one or more healthy anatomy parts in the 3D image or a 3D model based on the 3D image so as to close at least one diseased part in the 3D image or the 3D model based on the 3D image.

8. The method of claim 1, wherein designing the 3D model of the vascular endoprosthesis comprises identifying stable landing zones in the 3D image or corrected 3D model of the region of the patient's lumen anatomy.

9. The method of claim 8, wherein identifying stable landing zones comprises selecting one or more anatomical regions in the 3D image or corrected 3D model of the region of the patient's lumen anatomy showing greater stability in time.

10. The method of claim 1, wherein designing the 3D model of the vascular endoprosthesis comprises identifying branching vessels in the 3D image or corrected 3D model of the region of the patient's lumen anatomy and providing holes in the 3D model of the vascular endoprosthesis configured to direct blood flow towards said branching vessels.

* * * * *